United States Patent [19]

Saito et al.

[11] 4,395,487

[45] Jul. 26, 1983

[54] METHOD FOR ASSAY OF α-AMYLASE ACTIVITY

[75] Inventors: Narimasa Saito; Tatsuo Horiuchi, both of Noda, Japan

[73] Assignee: Noda Institute for Scientific Research, Noda, Japan

[21] Appl. No.: 256,194

[22] Filed: Apr. 21, 1981

[30] Foreign Application Priority Data

May 8, 1980 [JP] Japan ................................. 55-59980

[51] Int. Cl.$^3$ ............................................. C12Q 1/40
[52] U.S. Cl. ........................................ 435/22; 435/18; 435/202
[58] Field of Search ....................... 435/22, 14, 18, 25, 435/26, 28, 202, 203

[56] References Cited

U.S. PATENT DOCUMENTS

| | | | |
|---|---|---|---|
| 3,869,348 | 3/1975 | Gindler | 435/22 |
| 3,879,263 | 4/1975 | Adams | 435/14 |
| 3,971,702 | 7/1976 | Maekawa et al. | 435/14 |
| 4,000,042 | 12/1976 | Adams | 435/14 |
| 4,172,765 | 10/1979 | Keyes | 435/14 |
| 4,304,854 | 12/1981 | Nix et al. | 435/25 X |

Primary Examiner—R. B. Penland
Attorney, Agent, or Firm—Schuyler, Banner, Birch, McKie & Beckett

[57] ABSTRACT

A method for the assay of α-amylase activity, which comprises adding an α-amylase-containing sample to maltohexaitol or maltohexaonic acid used as substrate, reacting, at the same time or subsequent to the addition, α-glucosidase with the resulting mixture, and determining the reaction product to assay the α-amylase activity.

6 Claims, 2 Drawing Figures

METHOD FOR ASSAY OF α-AMYLASE ACTIVITY

This invention relates to a method for the assay of α-amylase activity by use of maltohexaitol or maltohexaonic acid as substrate.

α-Amylase in the human body is produced mainly in the pancreas or salivary gland and the determination of the amount of α-amylase in the body fluids such as serum, urine and the like is a clinically useful means in the diagnosis. For instance, in normal healthy subjects the α-amylase activity in the serum is approximately constant, whereas in patients suffering from acute pancreatitis it increases in response to the pathological condition of the disease. Consequently, the α-amylase content of the serum is an important clinical parameter for the pancreatic function.

For the assay of α-amylase activity various methods have been known, in which the iodine-starch reaction or turbidimetry is utilized or the amount of reducing sugar is determined. In these methods the α-amylase activity is assayed by allowing α-amylase to act on starch used as substrate and determining the rate of disappearance of the iodine-starch reaction, or the rate of decrease in turbidity of the dispersion of substrate starch or determining chemically or enzymatically the amount of reducing sugar formed by the reaction. However, the starch used in the above methods as substrate for the quantitative determination is difficult to obtain in constant quality at any time and, hence, the standardization of the method of assay becomes very difficult. Consequently, at each time of assay it becomes necessary to perform the assay on a sample as well as on a standard sample. A method, in which the substrate starch is replaced by blue starch containing a combined chromogenic material, is also in actual use, though not widely. Because of the necessity of centrifugal separation in its procedure, this method has disadvantages in that the method is not suited for automation, and makes it difficult to measure the rate of reaction between the substrate and the α-amylase by the method of rate assay.

In determining the α-amylase content of a sample it is necessary to select a substrate which answers the requirements that it should be easily decomposable by α-amylase and it should be a water-soluble low molecular weight compound having a definite structure which will not interfere with the stoichiometry of the reaction (i.e. it should be split at a definite position in the molecule of substrate). For the substrate which substantially answer the said requirements, there have been proposed maltotetraose ($G_4$) and maltopentaose ($G_5$) [Japanese Patent Application "Kokai" (Laid-open) No. 56,998/1975; U.S. Pat. No. 3,879,263]. Of these substrates, $G_4$ has disadvantages in that it is fairly inferior in the reactivity to α-amylase and gives a high blank value, requiring a blank test at each time of assay, while $G_5$ is higher in reactivity than $G_4$ but has drawbacks in that the reactivity to α-amylase is still insufficient and the blank value seems to be also still high in an assay procedure coupled with α-glucosidase.

It has also been proposed to use as substrates maltohexaose ($G_6$) (U.S. Pat. No. 4,000,042), oligosaccharides having higher molecular weights than that of $G_6$, or modified oligosaccharides having their reducing terminal hydroxyl groups replaced by aromatic groups. Such substrates are subject to splitting at two or more α-1,4-lycoside linkages in a molecule by the action of α-amylase, meaning that the product formed by the reaction between α-amylase and the substrate behaves again as a substrate for the enzyme, resulting in disturbance of stoichiometry of the reaction. Such a substrate, therefore, cannot be called a suitable substrate for the rate assay.

Under the circumstances, the present inventors carried out extensive research on the method for determining the α-amylase activity with sufficient precision and rapidity. As a result, it was found that the α-amylase activity may be assayed with a high precision in a short period of time using as substrate maltohexaitol or maltohexaonic acid obtained by reducing or oxidizing in a customary way the hydroxyl group at the reducing terminal of maltohexaose ($G_6$). On the basis of this finding, the present invention has been accomplished.

An object of this invention is to provide a novel method for the assay of α-amylase activity.

Other objects and advantages of this invention will become apparent from the following description.

According to this invention, there is provided a method for the assay of α-amylase activity, which comprises adding a α-amylase-containing sample to maltohexaitol or maltohexaonic acid used as substrate, reacting, at the same time or subsequent to the addition, α-glucosidase with the resulting mixture, and determining the reaction product, glucose.

The accompanying drawings show the relationships between the increment of absorbance at 340 nm (ΔE/minute) and the α-amylase activity (Somogyi unit/dl) of the sample used in Example;

Figure 2:
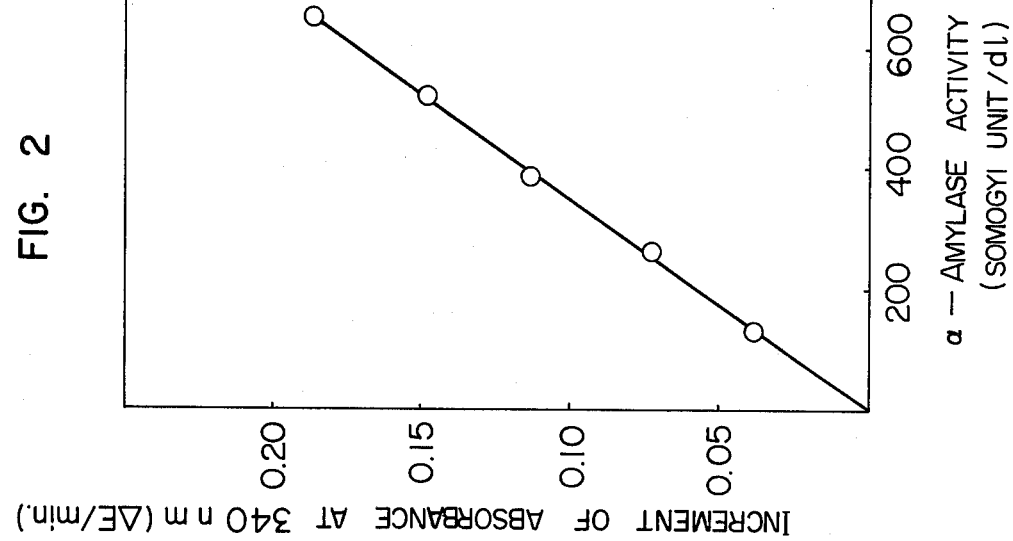
FIG. 2 is the case where maltohexaonic acid is used as substrate.

The invention is described below in detail.

The maltohexaitol to be used as substrate in the present method may be obtained according to the method of Abdel-Akher et al. [J. Amer. Chem. Soc., 73, 4691 (1951)] by reducing maltohexaose with a potassium borohydride solution at room temperature for 24 hours. The maltohexaonic acid may be obtained according to the method of Ingres and Israel [J. Chem. Soc., 810 (1948)] by oxidizing maltohexaose with a sodium hypoiodite solution (pH 11) at room temperature for one hour.

The method of assaying α-amylase activity by the use of maltohexaitol or maltohexaonic acid as substrate according to this invention may be described by the following reaction schemes:

(A) The case where maltohexaitol is used as substrate:

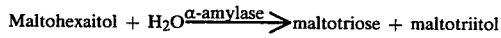

Maltohexaitol + H$_2$O $\xrightarrow{\alpha\text{-amylase}}$ maltotriose + maltotriitol

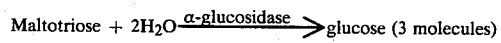

Maltotriose + 2H$_2$O $\xrightarrow{\alpha\text{-glucosidase}}$ glucose (3 molecules)

Maltotriitol +

2H$_2$O $\xrightarrow{\alpha\text{-glucosidase}}$ glucose (2 molecules) + sorbitol (B) The case where maltohexaonic acid is used as substrate:

Maltohexaonic acid +

-continued

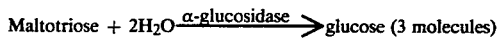

Maltotrionic acid +

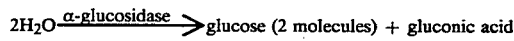

According to the above reaction schemes, 5 molecules of glucose and one molecule of sorbitol are formed from one molecule of maltohexaitol, while 5 molecules of glucose and one molecule of gluconic acid are formed from one molecule of maltohexaonic acid. The amount of glucose is determined by any of the following methods:

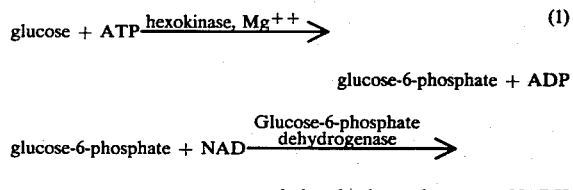

Note:
ATP = adenosine triphosphate
ADP = adenosine diphosphate
NAD = β-nicotinamide adenine dinucleotide
NADH = reduced β-nicotinamide-adenine dinucleotide The amount of NADH formed in the above reaction is determined spectro-photometrically from the increment of absorbance at 340 nm.

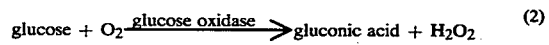

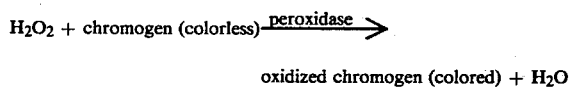

The amount of glucose in the reaction mixture may be determined by measuring spectrophotometrically the increment of absorbance at the wavelength characteristic of the oxidized coloring substance formed by the above reaction.

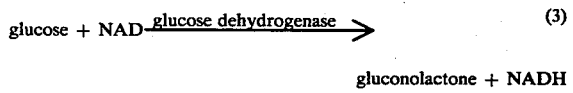

The amount of glucose in the reaction mixture may be determined, as in (1), by measuring spectrophotometrically the amount of NADH formed by the above reaction from the increment of absorbance at 340 nm.

The advantages of using maltohexaitol or maltohexaonic acid as the substrate for quantitative determination according to this invention are as described below.
(a) Both substrates are easily soluble in water and have high reactivities to α-amylase.
(b) The stoichiometry of the reaction holds, because only the third α-1,4-glucosidic linkage from the sorbitol or gluconate residue is split. The maltotriose, maltotriitol or maltotrionic acid easily undergoes splitting by the action of α-glucosidase to form glucose.
(c) With either substrate, the blank value can be made as small as substantially negligible.

The sample to be assayed by the method of this invention can be of any of those containing α-amylase, such as, for example, serum, blood, urine, and the like.

The α-glucosidase to be used in the present method may be derived from animals, vegetables, or microorganisms. Above all, α-glucosidase originated from yeast is preferred.

The α-glucosidase can be added to the reaction system either simultaneously with the addition of an α-amylase-containing sample to the substrate (maltohexaitol or maltohexaonic acid) or at a suitable moment during the period from the addition of sample to the completion of the reaction.

The reaction under pH conditions of generally 5 to 9, preferably 6.5 to 7.5 is advantageous for the curtailment of reaction time and the improvement in the precision of assay.

The buffer to be used in adjusting pH of the reaction system can be any of those capable of adjusting to pH 5-9, such as, for example, β-glycerophosphate, tris-acetate or barbital-HCl, or an inorganic phosphate such as Sörensen.

It is also possible to add to the reaction system a suitable activator for α-amylase, such as, for example, sodium chloride, potassium chloride or calcium chloride.

The present invention is very significant for the industry, because it allows the assay of α-amylase activity in an α-amylase-containing sample in a shorter period of time with better precision as compared with the conventional methods, the blank value being as small as substantially negligible.

The invention is further illustrated below in detail with reference to Example, but the invention is not limited thereto.

EXAMPLE

For an α-amylase-containing sample, a serum having an α-amylase activity of 650 Somogyi units/dl was prepared by adding to a serum originated from a normal healthy subject equal amounts of partially purified α-amylases from human salivary gland and from human pancreas. The resulting serum was successively diluted with physiological saline to prepare a series of samples having varied α-amylase activities (cf. FIGS. 1 and 2). The α-amylase activity was expressed in accordance with the saccharogenic method (i.e. Somogyi method) described in "Clinical Chemical Analysis IV," p. 21–39 (published by Tokyo Kagaku Dojin Co., 1970): 1 unit of α-amylase activity corresponds to the amount of the enzyme which release 1 mg of reducing sugar (as glucose equivalent) by the reaction between α-amylase and soluble starch at pH 6.9 and 40° C. for 30 minutes.

To 0.02 ml (per test plot) of the above sample, was added 1.4 ml (120μmoles) of β-glycerophosphate buffer (pH 7.0). After standing for 2 minutes at 37° C., the mixture was admixed with the following reagents: hexokinase, 1.0 U/0.1 ml; glucose-6-phosphate dehydrogenase, 3.0 U/0.1 ml; ATP, 1.0 mg/0.1 ml; NAD, 1.5 mg/0.1 ml; MgCl$_2$-NaCl, 0.475 mg-1.17 mg/0.04 ml. The resulting mixture was incubated for 2 minutes at 37° C. to admit consumption of the glucose in the sample.

To the above solution, were added 4 mg/0.1 ml of maltohexaitol and 30 U/0.04 ml of α-glucosidase. The reaction was allowed to start at 37° C. and the mixture was incubated for 5 minutes while measuring at one minute interval the increment of the absorbance at 340 nm. The mean value of the increment of absorbance per minute (ΔE/minute) was obtained after subtracting the blank value from the measured value (the blank value was within the limit of error as will be described later). The mean values of the increment per minute were plotted in FIG. 1.

The above procedure was repeated, except that maltohexaonic acid was used in place of the maltohexaitol. The mean values of the increments per minute of the absorbance (ΔE/minute) were plotted in FIG. 2.

The blank value was determined in the same manner as above, except that an identical volume of physiological saline was used in place of the serum. All of the blank values were within the limit of error, that is, below 0.001.

Figure 1:
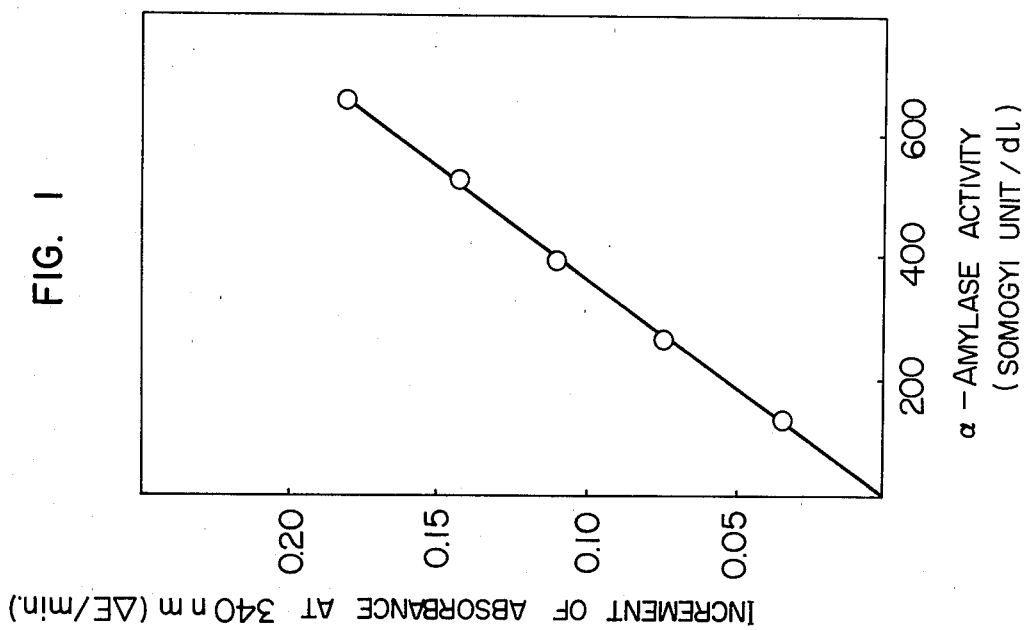
FIG. 1 represents the case where maltohexaitol is used as substrate.

FIGS. 1 and 2 show that in determining the α-amylase content of a sample by using maltohexaitol or maltohexaonic acid as substrate, the reaction completes in a short period of time owing to a high reactivity of the substrate to α-amylase, and that the relationship between the increment per minute of the absorbance (ΔE/minute) and the α-amylase activity (in Somogyi unit/dl) is represented by a straight line; that is, said increment is proportional to the α-amylase activity so that the assay of α-amylase activity may be carried out rapidly and precisely.

In the next experiment, the α-amylase-containing sample prepared above (the sample having an α-amylase activity of 650 Somogyi units/dl prepared by adding to a serum originated from a normal healthy subject equal amounts of partially purified α-amylase from human salivary gland and that from human pancreas) was allowed to act, as in the preceding experiment described above, on various substrates shown in Table 1. The results of assay of α-amylase activity and the blank values were shown in Table 1.

TABLE 1

| Substrate | α-amylase activity | | |
|---|---|---|---|
| | Found (E/min.) | Blank value (E/min.) | Increment of absorbance (ΔE/min.) |
| Maltohexaonic acid | 0.187 | 0.000 | 0.187 |
| Maltohexaitol | 0.181 | 0.000 | 0.181 |
| Maltotetraose | 0.074 | 0.034 | 0.040 |
| Maltopentaose | 0.102 | 0.005 | 0.097 |
| Maltohexaose | 0.072 | 0.002 | 0.070 |
| Maltoheptaose | 0.033 | 0.001 | 0.032 |
| Maltopentaitol | 0.014 | 0.001 | 0.013 |
| Maltoheptaitol | 0.035 | 0.000 | 0.035 |

The purity of each substrate shown in Table 1 was 99.5% (W/W) or above.

As is apparent from Table 1, when the α-amylase activity of a sample was assayed by using maltohexaitol or maltohexaonic acid as substrate, as compared with other substrates, the reaction time could be much reduced because of higher reactivities to α-amylase (larger increments of absorbance); the blank values were found to be negligible in the case of said compounds.

What is claimed is:

1. A method for the assay of α-amylase activity, which comprises adding an α-amylase-containing sample to maltohexaitol or maltohexaonic acid used as substrate, reacting, at the same time or subsequent to the addition, α-glucosidase with the resulting mixture, and determining the reaction product to assay the α-amylase activity.

2. A method according to claim 1, wherein the α-amylase-containing sample is serum, blood or urine.

3. A method according to claim 1, wherein the assay of α-amylase activity is carried out at pH 5-9.

4. A method according to claim 3, wherein the pH is adjusted with β-glycerophosphate or an inorganic phosphate.

5. A melthod according to claim 1, wherein sodium chloride, potassium chloride or calcium chloride is added as an activator for the α-amylase.

6. A method according to claim 1, wherein the α-glycosidase is originated from yeast.

* * * * *